United States Patent [19]

Wehrmeister

[11] 4,260,634

[45] Apr. 7, 1981

[54] ANTIMICROBIAL AGENTS

[75] Inventor: Herbert L. Wehrmeister, Terre Haute, Ind.

[73] Assignee: International Minerals & Chemical Corp., Terre Haute, Ind.

[21] Appl. No.: 49,694

[22] Filed: Jun. 18, 1979

[51] Int. Cl.$^3$ .................... A01N 33/02; A01N 37/18
[52] U.S. Cl. ................................. 424/324; 424/330; 564/219; 564/341
[58] Field of Search ............................. 424/324, 330; 260/562 R, 570.5 S

[56] References Cited

U.S. PATENT DOCUMENTS

| | | | |
|---|---|---|---|
| 2,434,099 | 1/1948 | Bousquet | 260/570.5 S |
| 2,769,839 | 11/1956 | Finehe | 260/570.5 S |
| 2,773,899 | 12/1956 | Martin et al. | 260/570.5 S |
| 3,318,953 | 5/1967 | Wehrmeister | 260/558 |

OTHER PUBLICATIONS

Wehrmeister, J. Org. Chem., 28 (1963) 2589–2591.
Pagani et al., C.A., vol. 68 (1968) 39259v.

*Primary Examiner*—Allen J. Robinson
*Attorney, Agent, or Firm*—Robert H. Dewey

[57] ABSTRACT

Certain phenylthioalkylamines and amides thereof are antifungal or antibacterial agents, or both, and provide a method of controlling the growth of these microorganisms.

2 Claims, No Drawings

ANTIMICROBIAL AGENTS

BACKGROUND OF THE INVENTION

This invention relates to antimicrobial agents. In a particular aspect, this invention relates to antimicrobial compositions useful for controlling the growth of fungi and bacteria.

One of the problems in metalworking industries is the suceptibility of metalworking fluids (which are emulsions of oil or chemical lubricants in water) to microbial attack. Were it not for this microbial contamination, the oil could be used for many months, but actually the microbial growth shortens the working life of the oil considerably. Microbial action may cause the emulsion to break and become acidic, thus causing corrosion problems. Some of the microbes may be pathogenic which can cause skin infections and other industrial health problems. In addition the microbial mycelia can clog pumps and valves, and often a foul odor develops. In a large installation, frequent replacement of metalworking fluids is costly.

SUMMARY OF THE INVENTION

It is an object of this invention to provide antimicrobial agents.

It is another object of this invention to provide antimicrobial agents useful for controlling the growth of fungi and bacteria.

Other objects will be apparent to those skilled in the art from the disclosure herein.

It is the discovery of the present invention to provide a method of controlling the growth of microorganisms by applying to them or to the environment inhabited by them a compound represented by the formula:

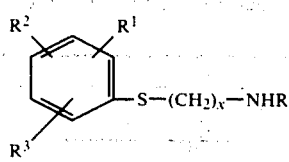

where R can be hydrogen or alkyl of 1 to 3 carbon atoms, acetyl or propionyl; $R^1$ and $R^2$ can be hydrogen or halogen, e.g. chlorine or bromine, and can be the same or different; and $R^3$ can be hydrogen or halogen, e.g. chlorine or bromine, or alkyl of 1 to 3 carbon atoms and x is 2 or 3. When R is hydrogen, a salt of the compound with a strong acid can also be used. It is also an embodiment of this invention to provide compounds of the above formula wherein at least one of $R^1$, $R^2$ or $R^3$ is other than hydrogen.

DETAILED DISCUSSION

The compounds of the present invention are effective for controlling the growth of a wide variety of microorganisms. They are generally effective to combat the growth of microorganisms at a concentration of at least about 500 ppm. However, depending on the vigor of the organisms, the length of time during which growth should be suppressed, etc., concentrations of about 1000 ppm or even up to 1500 or 2000 ppm may be preferred.

The compounds used in the practice of the present invention can be prepared by the method of H. L. Wehrmeister (J. Org. Chem. 28, 2589 (1963) and U.S. Pat. No. 3,318,953, which is incorporated herein by reference thereto), namely by reacting an alkanolamine with an arylmercaptan and a lower alkanoic acid in about a 1:1:1 mole ratio, thereby obtaining the amide. Preferably the reaction is conducted at elevated temperature. The amide so formed is then separated from the reaction mixture, preferably by distillation at reduced pressure.

The amides are useful antimicrobial agents, but they can also be hydrolyzed to the amine by heating in the presence of a strong acid. Suitable acids include but are not limited to mineral acids such as hydrochloric and sulfuric, and also strong organic acids such as trichloroacetic, p-toluene sulfonic acid and the like. The salts have antimicrobial properties and may be used in the practice of this invention. However, the free amine is sometimes more active and may be preferred. The free amine is separated from the salt by treatment with a strong alkali, e.g. sodium hydroxide. The formation of the amide and the free amine are discussed in detail in the following examples and also in U.S. Pat. No. 3,318,953.

The method of controlling the growth of microorganisms of this invention comprises application of an antimicrobial compound represented by the above formula to a substratum infested with the microorganisms to be controlled or to a substratum to be protected from infestation with the microorganisms. The term substratum as used herein is intended to mean the environment or medium upon which an organism grows and includes both animate and inanimate matter, such as animal and vegetable, living or dead, and the soil. The terms microbe and microorganism as used herein are intended to include bacteria and fungi. The term antimicrobial as used herein is intended to include the terms bactericidal, bacteriostatic, fungicidal and fungistatic. No attempt has been made to determine if the products actually cause the death of the organism or merely prevent their growth. The compounds are especially useful in cutting oils for metalworking, latex paints, and recirculated cooling water.

The compounds of this invention are water-soluble, at least to the extent that they are effective antimicrobials. Preferably they are supplied to the microorganisms or to the environment inhabited by them as an aqueous solution. However, they are also very soluble in organic solvents such as aliphatic alcohols and ketones and can be employed as a non-aqueous solution if desired. Also, if preferred, the compounds can be used as such without dilution.

In controlling the growth of microorganisms the compounds of this invention are supplied to the organisms or to their environment in a lethal or toxic amount. This can be done by dispersing a compound or mixture thereof, or a composition containing it, in, on or over an environment or substratum infested with, or to be protected from, the microorganisms. A compound of this invention or a mixture containing it can be dispersed in any conventional method which permits contact between the organisms and the antimicrobial agents of this invention. The system to be protected may contain a compound of this invention added by the manufacturer at the time of manufacture or preparation. Alternatively, the proper amount of the compound can be added ad libitum.

The antimicrobial properties were determined by the tube dilution method. Media for the bacterial cultures was trypticase soya broth at pH 7.3 prepared as known in the art, and the media for the fungi was Sabouraud broth at pH 5.6, also prepared as known in the art. The inoculum was standardized by the pour plate method for a total viable organism count. The amount of the inoculum per tube was 5 ml at a population of $10^5$ organisms per ml.

The compounds were tested for antibacterial and antifungal activity against bacteria (both Gram positive and Gram negative) and fungi. The results are reported as minimum inhibitory concentration, which is the range between the highest concentration which permits growth and the lowest concentration which prevents growth. They increase exponentially. Because of uncontrollable variables, such as the vigor of the organism, the data are reproducible to about plus or minus one range.

The invention will be better understood with reference to the following examples. It is understood, however, that these examples are intended only to illustrate the invention and it is not intended that the invention be limited thereby.

EXAMPLE 1

N-Methyl-2-(phenylthio)ethylamine

A. 2-Methylaminoethanol 38 g (0.5 mole), propionic acid 37 g (0.5 mole) and benzenethiol 55 g (0.5 mole) were dissolved in 50 ml benzene in a 500 ml reaction vessel equipped with a distillation column and take-off head and a heat source. The mixture was heated at 81°–87° C. until 19.6 ml of water had been removed. The reaction mixture was then distilled through an 18" Vigreux column. A cut distilling at 137°–148° at 0.2 mm was taken as the product, N-methyl-2-(phenylthio)ethylpropionamide, a known compound. It was redistilled through an 18" glass helice-packed column and the cut distilling at 154°–158° at 0.05 mm was taken as the product. The infrared spectrum was consistent with the proposed structure. It analyzed 6.15% nitrogen and 14.71% sulfur compared with 6.27% and 14.35% respectively.

B. A portion of the amide, 44.7 g, was heated at reflux in 100 ml of concentrated HCl for 24 hours. The mixture was cooled and there was added 200 ml of 25% NaOH. The mixture was extracted with three 100 ml portions of benzene and the extract was dried with 20 g sodium sulfate. It was distilled through an 18" Vigreux column. The fraction distilling at 112°–112.5° at 4.0 mm was taken as the product. It analyzed 8.56% nitrogen and 20.95% sulfur (19.76% by another method) compared with 8.37% and 19.16% respectively for the proposed structure. The neutral equivalent found was 168.40 compared with a calculated molecular weight of 167.3.

The compound, N-methyl-2-(phenylthio)ethylamine, which was designated P-2089, was tested for antimicrobial activity by the tube dilution method, which is known in the art. The results obtained were as follows.

| BACTERIA | Minimum Inhibitory Conc., ppm |
| --- | --- |
| Bacillus subtilis | 65–125 |
| Staphylococcus aureus | 33–65 |
| Streptococcus faecalis | 125–250 |
| Sarc. lutea | 125–250 |
| Escherichia coli | >1000 |
| Aero. aerogenes | >1000 |
| Sal. typhii | >1000 |
| Desulfo. desulfuricans | 65–125 |
| FUNGI | |

-continued

| BACTERIA | Minimum Inhibitory Conc., ppm |
| --- | --- |
| Clad. herbarum | 65–125 |
| Cephalosporum sp. | 125–250 |
| Trichomonas ment. | 125–250 |
| Aspergillus niger | 500–1000 |
| Aureo. pullulans | 250–500 |
| Fus. moniliforme | <1000 |
| Sac. cerevisiae | 250–500 |
| Candida albicans | 250–500 |

Thus, as can be seen, the product is useful for controlling the growth of Gram positive bacteria and many fungi.

A cutting oil emulsion is prepared according to the following formula:

| Light mineral oil | 20 parts |
| --- | --- |
| Water | 76.9 |
| P-2089 | 0.1 |
| Emulsifying agent | 3 |
| | 100 |

The emulsion remains free from microbial contamination for a long period of time when used as a cutting oil.

EXAMPLE 2

A. N-[3-(p-Chlorophenylthio)propyl]propionamide

The experiment of Example 1A was repeated in all essential details except that p-chlorobenzenethiol 50 g (0.67 mole), 3-aminopropanol 40.9 g (0.67 mole) and propionic acid 49.6 g (0.67 mole) were reacted. There was obtained N-[3(p-chlorophenylthio)propyl]propionamide, m.p. 69°–70° C. It was designated P-2135 for convenience. The nmr spectrum was consistent with the proposed structure. It analyzed as follows:

| | C | H | N | 0 | S | Cl |
| --- | --- | --- | --- | --- | --- | --- |
| Calc. %: | 55.91 | 6.26 | 5.43 | 6.21 | 12.44 | 13.75 |
| Found, %: | 56.15 | 6.11 | 5.74 | 7.35 | 12.40 | 13.17 |

The minimum inhibitory concentration for bacteria was found to be above 1000 ppm and, therefore, relatively ineffective for controlling the growth of bacteria. However, the MIC was 100–500 ppm for the four species of fungi tested and was thus classed as effective for controlling the growth thereof.

B. 3-[p-Chlorophenyl)thio]propylamine Hydrochloride

The experiment of Example 1B was repeated in all essential details except that P-2135 was hydrolyzed. There was obtained 3-[p-chlorophenyl)thio]propylamine hydrochloride, m.p. 155°–157°. It was designated P-2141. The nmr spectrum was consistent with the proposed structure. The product analyzed as follows:

| | C | H | N | S | Cl |
| --- | --- | --- | --- | --- | --- |
| Calc., %: | 45.39 | 5.50 | 5.88 | 13.46 | 29.77 |
| Found, %: | — | — | 5.82 | 13.32 | 29.01 |

The minimum inhibitory concentration (MIC) was determined against seven species of bacteria and four species of fungi. It was 100–500 ppm in each case. The compound is thus effective for controlling the growth of bacteria and fungi.

EXAMPLE 3

A. N-[3-(p-Methylphenylthio)propyl]propionamide

The experiment of Example 1A was repeated in all essential details except that p-thiocresol, 3-aminopropanol and propionic acid in equimolar amounts were used as the reactants. There was obtained N-[3-(p-methylphenylthio)-propyl]propionamide, m.p. 55.5°–56.5° C., designated P-2142. The nmr spectrum was consistent with the proposed structure. P-2142 was generally ineffective for controlling the growth of seven species of bacteria but was effective (MIC-100–500) for controlling the growth of four species of fungi.

B. 3-[(p-Methylphenyl)thio]propylammonium Chloride

The experiment of Example 1B was repeated in all essential details except that P-2142 was the compound hydrolyzed. There was obtained 3-[(p-methylphenyl)thio]propylammonium chloride, m.p. 163°–164° C. It analyzed as follows:

|  | N | S | Cl |
|---|---|---|---|
| Calc., %: | 6.88 | 15.74 | 17.40 |
| Found, %: | 6.87 | 15.64 | 16.77 |

The compound was designated P-2149. The minimum inhibitory concentration was determined against eight species of bacteria. It was in the range of 500–1000 ppm for five of the eight species, but was relatively ineffective against Past. pseudotuberculosis, Pseud. aeruginosa, Shigella dysenteriae and four species of fungi.

C. 3-[(p-Methylphenyl)thio]propylamine

P-2149 was treated with sufficient sodium hydroxide solution to render it alkaline to litmus paper. The solution was then distilled and there was obtained 3-[(p-methylphenyl)thio]propylamine, b.p. 114°–116° at 0.6 mm. It was designated P-2150. The nmr spectrum was consistent with the proposed structure.

The minimum inhibitory concentration for seven species of bacteria was 100–500 ppm and was 500–1000 ppm against an eighth. The MIC for four species of fungi was 100–500. Thus, the free amine was widely effective for controlling the growth of bacteria and fungi.

EXAMPLE 4

A. N-(3-Phenylthiopropyl)acetamide

The experiment of Example 1A was repeated in all essential details except that benzenethiol, 3-amino-1-propanol and acetic in equimolar amounts were used as the reactants. There was obtained N-(3-phenylthiopropyl)acetamide; it was designated P-2147. It analyzed as follows:

|  | C | H | N | S |
|---|---|---|---|---|
| Calc., %: | 63.12 | 7.22 | 6.69 | 15.32 |
| Found, %: | 62.94 | 7.21 | 6.76 | 15.14 |

It was tested against eight species of bacteria and found to be ineffective for controlling the growth. However, the MIC for four fungi was 500–1000 ppm, so it is effective against fungi.

B. 3-Phenylthiopropylammonium Chloride

The experiment of Example 1B was repeated in all essential details except that P-2147 was the compound which was hydrolyzed. There was obtained 3-phenylthiopropylammonium chloride, m.p. 159°–160° C. It was designated P-2148. The nmr spectrum was consistent with the proposed structure and the compound analyzed as follows:

|  | N | S | Cl |
|---|---|---|---|
| Calc., %: | 6.88 | 15.74 | 17.40 |
| Found, %: | 6.87 | 15.64 | 16.77 |

When tested against eight species of bacteria, the MIC for seven was 500–1000 and thus was effective for controlling their growth. However, it was relatively ineffective against Shigella dysenteriae and four species of fungi.

3-Phenylthiopropylamine

The experiment of Example 3C is repeated in all essential details except that P-2148 is substituted for P-2149. There is obtained 3-phenylthiopropylamine. It is effective for controlling the growth of bacteria and fungi at low concentrations.

EXAMPLE 5

A. N-[3-(p-Bromophenylthio)propyl]propionamide

The experiment of Example 1A was repeated in all essential details except that p-bromobenzenethiol, 3-aminopropanol and propionic acid are the reactants. There is obtained N-[3-(p-bromophenylthio)propyl]propionamide, m.p. 64°–65.5°. The nmr spectrum was consistent with the proposed structure. The compound, which was designated P-2172, was ineffective against eight species of bacterium and one species of fungi (Candida albicans), but the MIC for three species of fungi was 50–1000 and is thus effective for controlling their growth.

B. 3-[(p-Bromophenyl)thio]propylamine Hydrochloride

The experiment of Example 1B was repeated in all essential details except that P-2172 was hydrolyzed. There was obtained 3-[(p-bromophenyl)thio]propylamine hydrochloride, m.p. 159°–162° C. It was designated P-2173. The nmr spectrum was consistent with the proposed structure. The MIC for eight species of bacteria and one fungus was 50–100 ppm and for three other fungi was 100–500 ppm. It was thus generally effective for controlling growth.

EXAMPLE 6

3-[(2,4,5- Trichlorophenyl)thio]propylamine Hydrochloride

The experiment of Example 1A was repeated in all essential details except that 2,4,5-trichlorobenzylthiol, 3-aminopropanol and propionic acid were used as the reactants. The resulting compound was hydrolyzed as described in Example 1B and there was obtained 3-[(2,4,5-trichlorophenyl)thio]propylamine hydrochloride, m.p. 156°–157° C. It was designated P-2162. The nmr spectrum was consistent with the proposed structure. P-2162 was tested against eight species of bacteria and four species of fungi. The MIC was 50–100 ppm for most of them, and 10-50 for the others. Accordingly, it is broadly effective for controlling growth.

I claim:

1. A method of controlling the growth of bacteria or fungi or both comprising applying to them an antimicrobial amount of a compound represented by the formula

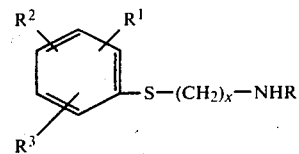

where R is acetyl or propionyl; $R^1$, $R^2$ and $R^3$ are hydrogen, and x is 2 or 3.

2. The method of claim 1 where R is acetyl.

* * * * *

UNITED STATES PATENT AND TRADEMARK OFFICE
CERTIFICATE OF CORRECTION

PATENT NO. : 4,260,634

DATED : April 7, 1981

INVENTOR(S) : Herbert L. Wehrmeister

It is certified that error appears in the above-identified patent and that said Letters Patent are hereby corrected as shown below:

Column 1, line 10, "suceptibility" should read -- susceptibility --

Column 6, line 22, "3-Phenylthiopropylamine" should read -- C. 3-Phenylthiopropylamine --

Signed and Sealed this

Twentieth Day of April 1982

[SEAL]

Attest:

GERALD J. MOSSINGHOFF

Attesting Officer   Commissioner of Patents and Trademarks